United States Patent [19]

Gortowski

[11] Patent Number: 4,943,370

[45] Date of Patent: Jul. 24, 1990

[54] METHOD AND APPARATUS FOR MONITORING MATERIAL IN A LIQUID

[75] Inventor: Edmund P. Gortowski, Louth, England

[73] Assignee: Conoco Inc., Ponca City, Okla.

[21] Appl. No.: 194,595

[22] Filed: May 16, 1988

[51] Int. Cl.$^5$ .............................................. C02F 1/40
[52] U.S. Cl. .................................. 210/85; 210/109; 210/521; 210/536; 210/745; 250/301
[58] Field of Search ................ 210/745, 800, 85, 94, 210/109, 110, 521, 536, 513; 250/301, 434, 435, 461.1

[56] References Cited

U.S. PATENT DOCUMENTS

| | | | |
|---|---|---|---|
| 2,263,108 | 7/1940 | Stuart | 250/71 |
| 2,490,642 | 12/1949 | Lipson | 250/83.6 |
| 2,852,693 | 9/1958 | Hughes et al. | 250/71 |
| 3,151,204 | 9/1964 | Stacy | 88/14 |
| 3,394,263 | 7/1968 | Baker | 250/223 |
| 3,493,304 | 2/1970 | Rovner | 356/103 |
| 3,500,046 | 3/1970 | Caldwell | 250/71 |
| 3,566,114 | 2/1971 | Brewer | 250/71.5 |
| 3,650,400 | 3/1972 | Warren et al. | 209/111.5 |
| 3,666,945 | 5/1972 | Frungel et al. | 250/71 R |
| 3,842,270 | 10/1974 | Gregory et al. | 250/301 |
| 3,933,654 | 1/1976 | Middelbeek | 210/521 |
| 3,965,920 | 6/1976 | deVial | 137/115 |
| 4,064,054 | 12/1977 | Anderson et al. | 210/536 |
| 4,103,167 | 7/1978 | Ellner | 250/432 R |
| 4,400,274 | 8/1983 | Protos | 210/521 |
| 4,554,074 | 11/1985 | Broughton | 210/521 |

FOREIGN PATENT DOCUMENTS

| | | |
|---|---|---|
| 949962 | 9/1956 | Fed. Rep. of Germany . |
| 2224310 | 12/1973 | Fed. Rep. of Germany . |
| 640568 | 7/1928 | France . |
| 994118 | 11/1951 | France . |
| 60-213842 | 10/1985 | Japan . |

Primary Examiner—Richard V. Fisher
Assistant Examiner—Christopher Upton
Attorney, Agent, or Firm—A. Joe Reinert

[57] ABSTRACT

An apparatus and method for monitoring the presence in a liquid of a material which is at lest partially immiscible in the liquid are disclosed. The apparatus includes a container and an overflow outlet for allowing a surface layer of the liquid to flow out of the container. A slick of the material forms in the container on a surface of the liquid. The container includes a settling portion with an adjustably angled baffle and a second, fixed baffle located therein, a concentrating portion for concentrating the slick downstream of the settling portion, and an intermediate constricting portion for gradually constricting the surface of the liquid. An ultraviolet light source and visible light detector are provided for detecting the fluorescent radiation produced by irradiating the surface of the liquid and the material.

7 Claims, 2 Drawing Sheets

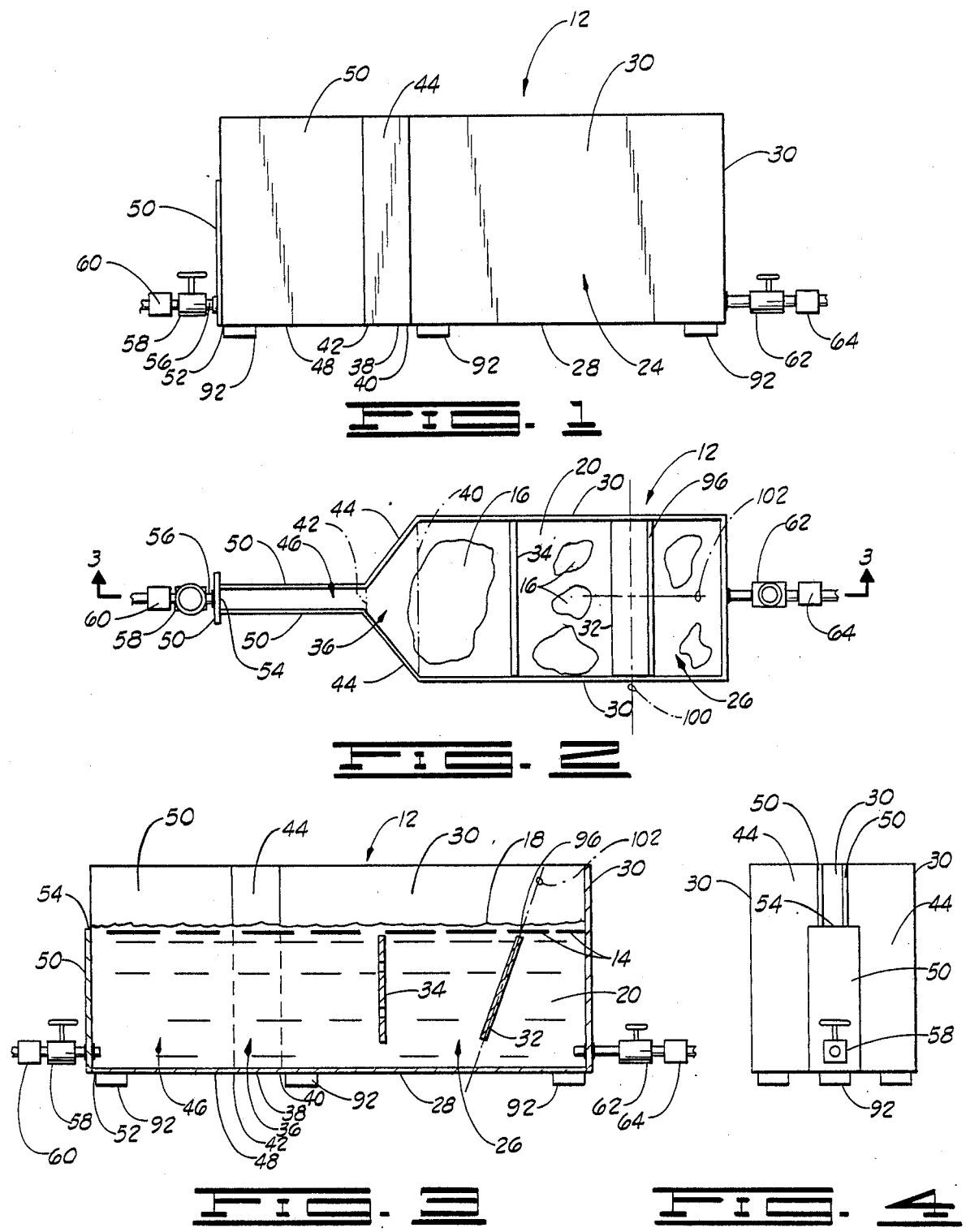

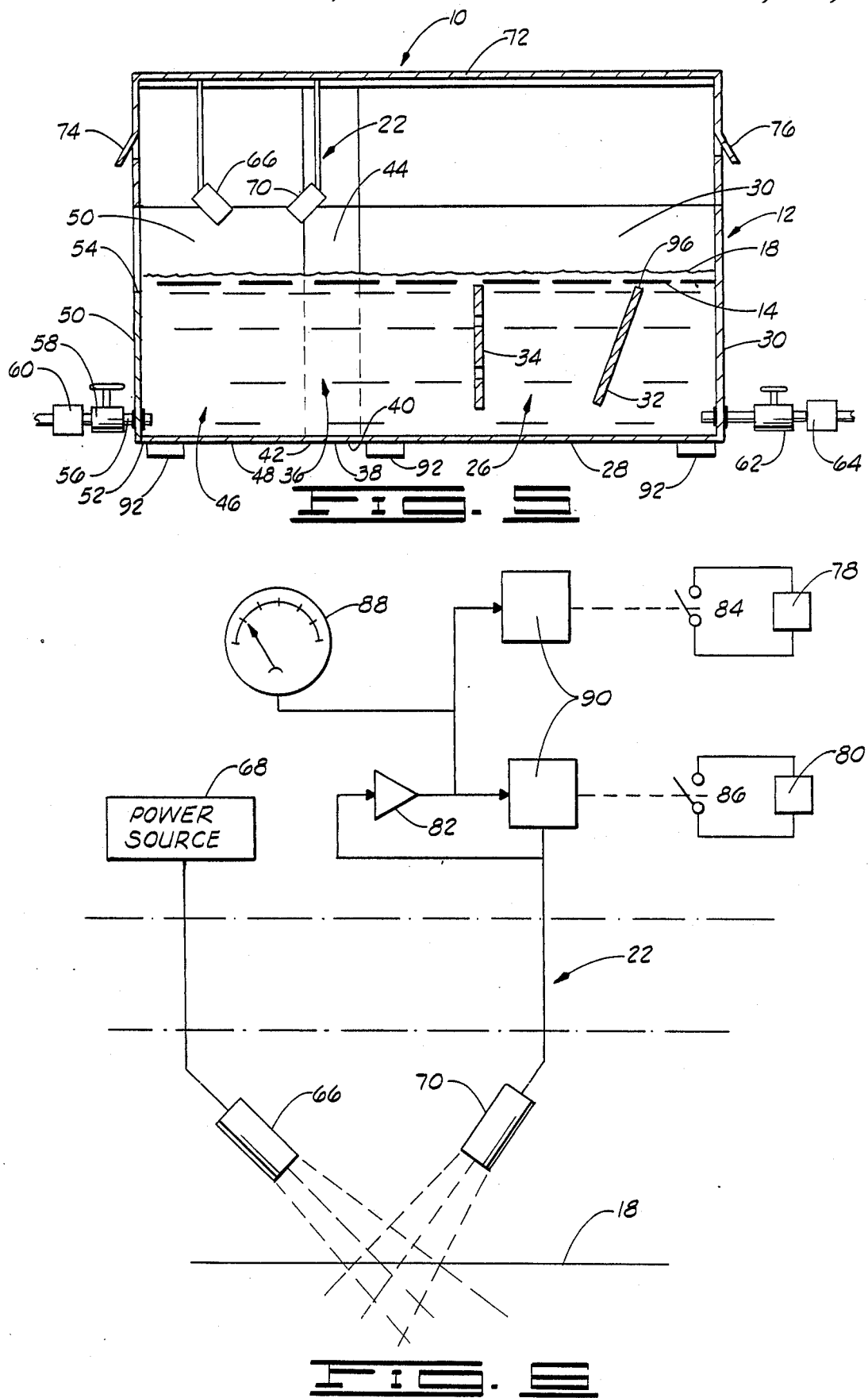

METHOD AND APPARATUS FOR MONITORING MATERIAL IN A LIQUID

BACKGROUND OF THE INVENTION

1. Field of the Invention

This invention relates generally to methods and apparatus for monitoring the presence of a material in a liquid, and more particularly, but not by way of limitation, to methods and apparatus for monitoring the presence in a liquid of a material which is at least partially immiscible in the liquid and which may be induced to form a slick on a surface of the liquid.

2. Description of the Prior Art

Previously issued patents disclose several methods and apparatus for monitoring the presence of a material in a liquid. A patent issued to Gregory et al., U.S. Pat. No. 3,842,270, discloses a method and apparatus for monitoring the presence in an aqueous medium of a material which fluoresces when exposed to ultraviolet light. The apparatus measures the fluorescent radiation caused by directing a beam of ultraviolet light into a falling stream of the aqueous based liquid containing the material to be monitored, and does so by employing visible light detecting means, an amplifier, and a recorder.

Patents to deVial, U.S. Pat. No. 3,965,920, and to Stuart, U.S. Pat. No. 2,263,108, disclose generally similar apparatus. The apparatus in the patent to deVial, as with the device described in the patent to Gregory, et al., employs a chamber having an inlet and an outlet for passing a stream of liquid therethrough, with a beam of ultraviolet light being directed against such a stream and fluorescence detection means for detecting fluorescent radiation produced thereby. Alarm means are also suggested for initiating an alarm when a predetermined level of fluorescent radiation is detected.

The patent to Stuart relates to a method and apparatus for detecting the presence of crude oil in drilling mud being circulated to the top of a well in the course of drilling the well. A beam of ultraviolet light is directed through a transparent window against a surface of the drilling mud returning from the bottom of the well at an angle with respect to the surface. A photosensitive cell is provided for detecting fluorescent emissions from crude oil in the mud.

A patent to Frungel et al., U.S. Pat. No. 3,666,945, discloses another variety of apparatus for monitoring a material in a liquid. In the patent to Frungel et al., a lamp for producing fluorescent radiation from a material and fluorescence detection means for detecting such fluorescent radiation are provided and located in the liquid or medium carrying the material to be monitored.

One problem encountered with devices such as are disclosed in the patents to deVial, Stuart, and Gregory et al. discussed above is the possibility of fouling of the optical equipment in those devices by the liquid or by the material to be monitored. Fouling of the optical equipment can lead to significant distortions in measurements of the material to be monitored, particularly when the material is present only in small concentrations in the liquid and therefore not as easily detected. Moreover, the possibility of fouling is likely increased where the liquid or medium carrying the material to be monitored is of a low viscosity, and therefore likely to be splashed, or where the material to be monitored has a marked affinity for glass or the like, as with oil. Fouling is likely also to be a problem with devices such as that disclosed in the patent to Frungel et al., where the optical equipment is located in the liquid or medium carrying the material to be monitored.

The problem of distorted measurements due to fouling becomes particularly significant when such devices as are discussed above are used to monitor industrial waste water for oleaginous materials and other potential environmental pollutants. It is frequently necessary in the monitoring of such pollutants to be able to monitor the presence of small concentrations of these pollutants, in that such concentrations may be toxic, or may be in excess of federally prescribed effluent guidelines. The fouling of the devices so used could necessitate, under such circumstances, shutting down an otherwise properly operating process until reliable measurements can be obtained to prevent exceeding federal guidelines and to prevent any potential pollution.

In the context of industrial processes involving the repeated or continuous discharge of an effluent stream, it may also be necessary to make a rapid series of tests or measurements to adequately monitor the presence of a pollutant or similar material in the effluent stream. Such might be the case where the flow rate of the effluent stream is high, or where the toxicity of the material is high.

As shown by the above-mentioned disclosures, there is a need for an apparatus and method that permit rapid and repeated monitoring for the presence of a material in a liquid, and that permit accurate monitoring of low concentrations of the material in the liquid.

Accordingly, it is an object of the present invention to provide an apparatus and method fulfilling this need, and which further permit accurate monitoring of low concentrations of the material in the liquid without excessive exposure to fouling.

It is a further object of the present invention to provide an apparatus and method that are easily manufactured, employed, and maintained.

Other objects and advantages will become more fully apparent from a consideration of the following description, the appended claims, and the accompanying drawings.

SUMMARY OF THE INVENTION

The present invention overcomes the above-noted and other shortcomings of the prior art by providing a novel and improved apparatus and method for monitoring a material in a liquid which permit rapid and repeated monitoring, and which further permit accurate monitoring of low concentrations of the material without excessive exposure to fouling.

The apparatus comprises slick-inducing means for inducing the material to form a slick on a surface of the liquid, and means for detecting the presence of the slick on the surface of the liquid. The term "slick" as used herein refers generally to an accumulation of a material to be monitored on a surface of a liquid, such as an accumulation of oil and petroleum products on the surface of a body of water.

The slick-inducing means of the present invention includes a container for receiving the liquid and overflow outlet means for allowing a surface layer of the liquid including the surface of the liquid where the slick is to be formed to flow out of the container.

The container provided by the present invention comprises a settling portion for reducing the turbulence of the liquid to be received, a concentrating portion for concentrating the slick downstream of the settling portion of the container, and an intermediate constricting portion for gradually constricting the surface of the liquid.

Control means for controlling the velocity of the surface of the liquid at variable flow rates of the liquid through the container is also provided, and comprises underflow outlet means, operably associated with the container, for draining liquid from the container in addition to that flowing out of the container via the overflow outlet means. Valve means operably associated with the underflow outlet means for controlling a rate at which the additional liquid is drained from the container by the underflow outlet means is also included.

A method for monitoring the presence in a liquid of a material which is at least partially immiscible in the liquid is described, and comprises inducing the material to form a slick on a surface of the liquid, as by reducing the turbulence of the liquid, and concentrating the slick for detection and measurement. The method preferably includes also gradually constricting the surface of the liquid, and monitoring the presence of the slick. Where the material fluoresces under ultraviolet light, this monitoring can be accomplished by irradiating the slick with ultraviolet light and detecting the fluorescent radiation from the slick.

BRIEF DESCRIPTION OF THE DRAWINGS

FIG. 1 is a side elevation view of the preferred embodiment of the slick-inducing means of the present invention.

FIG. 2 is a top plan view of the preferred embodiment.

FIG. 3 is a side sectional view of the preferred embodiment, taken along lines 3—3 in FIG. 2.

FIG. 4 is a left end view of the preferred embodiment of FIGS. 1–3.

FIG. 5 is a side sectional view, similar to FIG. 3, of the preferred embodiment, with the ultraviolet light source and fluorescence detection means positioned above the surface of the liquid.

FIG. 6 is a block diagram of the apparatus, with the alarm and control means operationally associated therewith.

DETAILED DESCRIPTION OF THE PREFERRED EMBODIMENT

Referring now to the drawings, the apparatus for monitoring material in a liquid is shown and generally designated by the numeral 10 (FIG. 5). In the preferred embodiment shown, the apparatus comprises slick-inducing means 12 for inducing a material 14 to form a slick 16 on a surface 18 of a liquid 20, and means for detecting the presence of the slick 16 on the surface 18 of the liquid 20, which means are generally designated by the numeral 22 (FIGS. 5 and 6).

Referring now to FIGS. 1–4, slick-inducing means 12 comprises a container 24 for receiving the liquid, and overflow outlet means 54 for allowing a surface layer of the liquid 20 including the surface 18 to flow out of the container 24.

The container 24 of the preferred embodiment comprises three portions. A settling portion 26 is provided in the container 24 for reducing the agitation or turbulence of the liquid 20 to be received, and comprises a settling base portion 28 of rectangular shape, a wall 30 extending upwardly from three sides of the settling base portion 28, an adjustably angled baffle 32 connected to the wall 30, and a second, fixed baffle 34 connected to the wall 30 downstream of the baffle 32 and substantially paralleling the baffle 32. Both baffles 32 and 34 are spaced above the settling base portion 28 of the container 24, as seen in FIG. 3.

The adjustable baffle 32 is shown as extending completely between the side walls 30, but it need not extend all the way to the side walls 30. Preferably, the adjustable baffle 32 is rotatable about a horizontal axis 100 (see FIG. 2) so as to divert incoming fluid upward or downward, and about an inclined axis 102 (see FIGS. 2 and 3) so as to divert incoming fluid toward one or the other of the side walls 30.

A constricting portion 36 for gradually constricting the surface 18 of the liquid 20 is also provided, and comprises a trapezoidal constricting base portion 38 having a first end 40 adjacent the settling portion 26 at the fourth side of the settling base portion 28 and tapering to a second end 42, and a wall 44 having two opposed portions extending upwardly from the nonparallel sides of the trapezoidal constricting base portion 38.

The third portion of the container 24 is a concentrating portion 46 for concentrating the slick 16 downstream of the settling portion 26. The concentrating portion 46 of the container 24 comprises a concentrating base portion 48 of rectangular shape, and a wall 50 having two opposed portions extending upwardly from the longer sides of the concentrating base portion 48, and having a portion extending upwardly from an outer end 52 of the concentrating base portion 48 relative to the settling portion 26. In the preferred embodiment, the overflow outlet means of the slick-inducing means 12 comprises a weir 54 defined in that portion of the wall 50 extending upwardly from the outer end 52 of the concentrating base portion 48. Although not shown in the drawings, a gutter or the like will typically be located below weir 54 to collect fluid flowing over weir 54 and to direct it to a drain.

The preferred embodiment of the apparatus 10 further comprises control means for controlling the velocity of the surface 18 of the liquid 20 at variable flow rates of the liquid 20 through the container 24. Such control means comprises underflow outlet means such as a conduit 56 operably associated with the container 24 for draining additional liquid 20 from the container 24, and valve means such as a valve 58 operably associated with the underflow outlet means 56 for controlling a rate at which the additional liquid 20 is drained from the container 24 by the underflow outlet means 56. For variable rates of addition of liquid 20 to the container 24, the underflow outlet means 56 and the valve means operate as means to drain additional liquid 20 from the container 24 at variable rates. These rates may be selected to correspond to a desired flow rate through the overflow outlet means of the apparatus 10, which flow rate in turn corresponds to a velocity of the surface 18 of the liquid 20 flowing through the weir 54. A flow indicator 60 is operably associated with the valve 58 to aid in consistently achieving a selected rate of flow through the underflow outlet means corresponding to a specific surface velocity at a given flow rate of the liquid 20 into the container 24.

The apparatus 10 of the preferred embodiment also comprises adjustable means for introducing various flow rates of the liquid 20 into the container 24, which adjustable means comprises a valve 62 connected to the container 24 adjacent the settling portion 26, and a flow indicator 64 operably associated with the valve 60 for measuring a volumetric flow rate of the liquid 20 through the valve 62.

The means 22 for detecting the presence of the slick 16 on the surface 18 of the liquid 20 is best described by reference to FIG. 6, and as shown comprises means for directing ultraviolet light against the surface 18 to produce fluorescent radiation from the material 14, such as a lamp 66 connected to a power source 68. Fluorescence detection means, such as a visible light detector or photocell 70, is provided also for detecting the fluorescent radiation produced by directing ultraviolet light against the surface 18 and the slick 16. An ultraviolet light source such as the lamp 66 is preferably positioned above the surface 18 of the liquid 20 so that ultraviolet light produced by the ultraviolet light source is directed against the surface 18 of the liquid 20 at an acute angle. Arrangement and construction of the lamp 66 and detector 70 so as to provide beam collimation and surface-only detection is desirable to avoid false readings from the fluorescense of any deposits of the material 14 on the base portions 28, 38, or 48, or on the walls 30, 44, or 50 of the container 24. The periodic removal of such deposits is also desirable as a further precaution against such false readings, as well as against the possibility of distortion of measurements due to a portion of such deposits being dislodged from the base portions or walls of the container 24 to become part of the slick 16. The positioning of the photocell 70 and the lamp 66 above the surface 18 of the liquid 20 as shown in FIG. 6 is further designed to prevent fouling of the photocell 70 or the lamp 66 by the liquid 20 or by the slick 16.

The photocell 70 and the lamp 66 of the preferred embodiment are connected to or otherwise associated with enclosure means, such as a cover 72, for preventing the incidence and possible interference of ambient light at the surface 18 of the liquid 20. The cover 72 is suitably equipped with vents 74 and 76 for the venting of any combustible or interfering vapors from the container 24.

As seen in FIG. 6, the preferred embodiment also comprises alarm means 78 and control means 80 operably associated with the lamp 66 and with the photocell 70 through an amplifier 82 for initiating an alarm and for altering a flow of the liquid 20, respectively, when a level of fluorescent radiation is detected. Where the apparatus 10 is used substantially as described earlier, i.e., in conjunction with the monitoring of industrial waste water for potential pollutants, then it is expected that the control means 80 would act to divert flow from the container 24 back for further treatment or to an alternate storage facility, and to otherwise prevent flow of the industrial waste water to the environment. The alarm means 78 and the control means 80 may be manually initiated with switches 84 and 86 by an operator of the apparatus 10 on observation of an output indicator 88, or may be initiated by the use of comparator circuits 90 at variable set-points of fluorescent radiation.

Finally, it was observed in testing of the apparatus 10 on an oil in water system that vibrations communicated to the apparatus 10 from its surroundings tended to interfere with the formation and continuity of a slick 16. Accordingly, in the preferred embodiment vibration absorbtion means such as the rubber feet 92 shown in FIGS. 1, 3, 4 and 5 are provided to prevent the transmittal of vibrations to the container 24 and the interference of those vibrations with the slick 16.

In the context of monitoring industrial waste water, such as that discharged from an offshore oil platform, for a potential pollutant such as oil, it is contemplated that the apparatus 10 described above may be used in various arrangements. First, all of the liquid 20 that is sought to be discharged may be directed through the container 24 prior to its discharge to the environment. In this arrangement, the apparatus 10 is preferably adjustable for various flow rates of the liquid 20 through the container 24.

Considering the example of using the apparatus 10 for monitoring the presence of oil in industrial waste water from an offshore oil platform, in this mode of operation the industrial waste water will enter the container 24 through the valve 62 and through the flow indicator 64 operably associated therewith for measuring the volumetric flow rate of the liquid 20 through the valve 62. For a flow rate of the liquid 20 through the valve 62, the valve 58 will be adjusted to produce a relatively slow surface velocity of the surface 18 of the liquid 20 over the weir 54.

Adjusting the valve 58 so that the velocity of the surface 18 of the liquid 20 through the container 24 and over the weir 54 is relatively slow will permit the movement of the oil from within the water, and the accumulation of the oil on a surface 18 of the water to form a slick 16.

In the oil in water system, the slick 16 is formed in part by the upward movement of the oil through the water in the settling portion 26 toward the relatively slow-moving surface 18 of the water. The surface 18 of the water, and thus the forming oil slick 16, are gradually constricted in the constricting portion 36 of the container 24, thus preventing sudden increases in the velocity of the surface 18 and in the turbulence of the water entering the concentrating portion 46 of the container 24 which could disrupt or disturb the slick 16.

The slick 16 is then concentrated in the concentrating portion 46 of the container 24 by the reduced width of the concentrating portion 46 prior to being discharged over the weir 54. The lamp 66 and the photocell 70 operate to produce and detect fluorescent radiation from the oil comprising the slick 16 prior to the discharge of such oil over the weir 54. The alarm means 78 and/or control means 80 are activated if the level of fluorescent radiation detected exceeds a value corresponding to a known and undesirable concentration of oil in water, or in general terms, of material in the liquid. Such a value is conventionally determined by calibrating the apparatus for various samples of known oil content.

The baffles 32 and 34 primarily operate to reduce the turbulence of the water as it flows through the container 24 so as to induce the smooth surface flow regime conducive to formation of the slick 16. Adjustably angled baffle 32 is specifically provided for helping to make the apparatus 10 adjustable for various flow rates of the liquid 20 through the container 24. The adjustably angled baffle 32 is designed especially to prevent any "dead spot" recirculation of the liquid 20 in the settling portion 26 of the container 24. Such "dead spot" recirculation can occur, as is well known, if the first baffle in the container 24 that is encountered by the liquid 20 is too vertically oriented. The extent to which the first baffle must be rotated about axis 100 and/or axis 102 depends on the flow rate of the liquid 20 through the container 24.

Tests on an oil in water system have indicated that a slight pivoting of the baffle 32 about horizontal axis 100, so that the top 96 of the baffle 32 is moved slightly upstream with respect to the flow of the water through the container 24, is best for helping to induce the formation of the slick 16 of oil in the water.

An alternative arrangement employing the apparatus 10 would direct only a portion of the effluent water from the platform through the container 24. In this arrangement, the overflow outlet means could be used exclusively for the discharge of the effluent water from the container 24, provided the inlet flow rate is set sufficiently low to produce the relatively slow surface velocity of the surface 18 over the weir 54 that is typically required for the proper formation of the slick 16. The underflow outlet means and the valve 58 operably associated with such underflow outlet means could then be omitted entirely from the apparatus 10, or merely closed. Further, the adjustably angled baffle 32 could be set at the proper angle for such an inlet flow rate.

Use of the apparatus 10 to receive only a portion of the total flow from a platform to the sea, or of the effluent from a facility generally, also permits either continuous or periodic sampling of effluent water. A periodic sampling capability may be useful, for instance, where it can be assumed that a given volume of effluent water has the same oil content as a sample volume to be run through the container 24. Where this assumption may be made, a sample of the effluent water is run through the container 24 and monitored. When it is ascertained whether the sample is within the prescribed limits, then the volume of water or liquid 20 of which the sample is representative may be suitably discharged or subjected to further treatment. When the next volume of water is sought to be monitored or tested, a sample is introduced into the container 24, and a sufficient time is permitted for the slick 16 formed from the new sample volume to displace the slick 16 from the old sample prior to detection.

In the oil in water system tested, the delay between the occurrence of a surge in the oil content of the incoming water and when the detection of that surge can be detected in the form of a slick 16 has been generally determined to be very short, normally in the order of seconds, and will typically depend principally on the length of the container 24 and the velocity of the surface 18 of the water carrying the slick 16. It is expected that some slight variation in response times, however, will occur depending on such other considerations as temperature for a given combination of a material and liquid, and that other combinations of materials and liquids may have shorter or longer response times than the oil in water example under the same general circumstances.

While a preferred embodiment of the invention has been described for the purpose of this disclosure, numerous changes in the construction and arrangement of parts can be made by those skilled in the art, which changes are encompassed within the spirit of this invention, as defined by the appended claims.

What is claimed is:

1. An apparatus for monitoring the presence in a liquid of a material which is at least partially immiscible in the liquid, comprising:
    a slick inducing means for inducing the material to form a slick on the surface of the material which comprises:
    a container for receiving the liquid which comprises:
    a settling portion for reducing the turbulence of the liquid to be received;
    a concentrating portion for concentrating said slick down-stream of said settling portion; and
    an intermediate constricting portion for gradually constricting said surface of the liquid;
    overflow outlet means for allowing a surface layer of said liquid including said surface to flow out of said container;
    means for detecting the presence of said slick on said surface of the liquid; wherein said settling portion comprises:
    a settling base portion;
    a wall extending upwardly from said settling base portion;
    an adjustably angled baffle disposed in said settling portion; and
    a second, fixed baffle disposed in said settling portion downstream of said adjustably angled baffle.

2. The apparatus as defined in claim 1, wherein said settling base portion comprises a rectangle.

3. The apparatus as defined in claim 1, wherein said adjustably angled baffle is spaced above said settling base portion.

4. An apparatus for inducing a material which is at least partially immiscible in a liquid to form a slick on a surface of the liquid, comprising:
    a container for receiving the liquid which comprises:
    a settling portion for reducing the agitation of the liquid to
    be received
    wherein said settling portion comprises:
    a settling base portion;
    a wall extending upwardly from said settling base portion;
    an adjustably angled baffle disposed in said settling portion; and
    a second, fixed baffle disposed in said settling portion downstream of said adjustably angled baffle;
    a concentrating portion for concentrating the slick downstream of said settling portion;
    an intermediate constricting portion for gradually constricting the surface of the liquid;
    overflow outlet means for allowing a surface layer of said liquid including said surface to flow out of said container; and
    control means for controlling the velocity of said surface of the liquid at variable flow rates of the liquid through said container, wherein said control means comprises;
    underflow outlet means, operably associated with said container, for draining additional liquid from said container; and
    valve means, operably associated with said underflow outlet means, for controlling a rate at which said additional liquid is drained from said container by said underflow outlet means.

5. The apparatus as defined in claim 4, wherein said settling base portion comprises a rectangle.

6. The apparatus as defined in claim 4, wherein said adjustably angled baffle is spaced above said settling base portion.

7. In an apparatus for monitoring the presence in a liquid of a material which fluoresces when irradiated by ultraviolet light, which material is at least partially immiscible in the liquid, and which material may be induced to form a slick on a surface of the liquid, a container for receiving the liquid; wherein the container comprises; a settling portion for reducing the agitation of the liquid to be received, a concentrating portion for concentrating said slick downstream of said settling portion, and an intermediate constricting portion for gradually constricting said surface of the liquid; overflow outlet means for allowing a surface layer of said liquid including said surface to flow out of said container; and control means for controlling the velocity of said surface of the liquid at variable flow rates of the liquid through said container; wherein said settling portion comprises;
  a settling base portion;
  a wall extending upwardly from the settling base portion;
  an adjustably angled baffled disposed in said settling portion; and
  a second, fixed baffle disposed in said settling portion downstream of said adjustably angled baffle.

* * * * *